United States Patent
Pamelard et al.

(10) Patent No.: US 10,013,598 B2
(45) Date of Patent: Jul. 3, 2018

(54) METHOD FOR PROCESSING MOLECULAR IMAGING DATA AND CORRESPONDING DATA SERVER

(71) Applicant: IMABIOTECH, Loos (FR)

(72) Inventors: Fabien Pamelard, Armantieres (FR); Jonathan M. Stauber, Haubourdin (FR)

(73) Assignee: IMABIOTECH, Loos (FR)

(*) Notice: Subject to any disclaimer, the term of this patent is extended or adjusted under 35 U.S.C. 154(b) by 77 days.

(21) Appl. No.: 15/110,430

(22) PCT Filed: Jan. 9, 2015

(86) PCT No.: PCT/FR2015/050051
§ 371 (c)(1),
(2) Date: Jul. 8, 2016

(87) PCT Pub. No.: WO2015/104512
PCT Pub. Date: Jul. 16, 2015

(65) Prior Publication Data
US 2016/0335473 A1    Nov. 17, 2016

(30) Foreign Application Priority Data
Jan. 10, 2014 (FR) ..................... 14 50176

(51) Int. Cl.
*G06K 9/00* (2006.01)
*G06F 19/26* (2011.01)
(Continued)

(52) U.S. Cl.
CPC .......... *G06K 9/0014* (2013.01); *G06F 19/26* (2013.01); *G06F 19/28* (2013.01); *G06T 3/40* (2013.01);
(Continued)

(58) Field of Classification Search
CPC ....... G06F 19/26; G06F 19/28; G06K 9/0014; G06T 3/40; G06T 7/0014; G06T 7/337;
(Continued)

(56) References Cited

U.S. PATENT DOCUMENTS 9,182,409 B2 * 11/2015 Stauber .............. G01N 33/6851
2003/0156136 A1 * 8/2003 Cattell ..................... G06F 19/26
715/771
(Continued)

FOREIGN PATENT DOCUMENTS

| CN | 101782930 A | 7/2010 |
| FR | 2 973 112 A1 | 9/2012 |
| WO | 2009/156897 A1 | 12/2009 |

OTHER PUBLICATIONS

Oshiaki Takai et al., "DGP: Dynamic grouping of particles for parallel molecular dynamics simulations," 2000, Systems and Computers in Japan, vol. 31, No. 9, pp. 10-17.*
(Continued)

*Primary Examiner* — Mekonen Bekele
(74) *Attorney, Agent, or Firm* — Young & Thompson

(57) ABSTRACT

A method for processing a plurality of spectral datasets (J1-Jn) intended for being used by a molecular imaging method or a method for recording a plurality of spectral datasets (J1-Jn), each spectral dataset (J1-Jn) being defined by a set of spatial positions (Xi, Yj) each of which is associated with a molecular spectrum with at least two dimensions containing a set of molecular information (S(Xi, Yj)), the method including in particular the following steps: for each dataset (J1-Jn), cutting the molecular spectrum associated with each position (Xi, Yj) into a plurality of spectrum segments (T1-Tm); inserting the segments (T1-Tm) obtained for each position (Xi, Yj) of each dataset (J1-Jn) into a database (BDD); selecting in the database (BDD), following a request relating to molecular informa-
(Continued)

tion of interest, the one or more segments (T1-Tm) containing the molecular information of interest; and selecting, within each segment (T1-Tm), the molecular information of interest.

18 Claims, 3 Drawing Sheets

(51) Int. Cl.
*G06F 19/28* (2011.01)
*G06T 3/40* (2006.01)
*G06T 7/00* (2017.01)
*H01J 49/00* (2006.01)
*G06T 7/33* (2017.01)
*G06T 7/90* (2017.01)

(52) U.S. Cl.
CPC ............ *G06T 7/0014* (2013.01); *G06T 7/337* (2017.01); *G06T 7/90* (2017.01); *H01J 49/0036* (2013.01); *G06T 2207/10088* (2013.01); *G06T 2207/10104* (2013.01); *G06T 2207/30024* (2013.01)

(58) Field of Classification Search
CPC ............ G06T 7/90; G06T 2207/10088; G06T 2207/10104; G06T 2207/30024; H01J 49/0036
See application file for complete search history.

(56) References Cited

U.S. PATENT DOCUMENTS

| | | | |
|---|---|---|---|
| 2008/0067420 A1* | 3/2008 | Laidevant | G01N 21/6408 250/459.1 |
| 2008/0309676 A1* | 12/2008 | Nehab | G06T 9/00 345/582 |
| 2009/0092301 A1* | 4/2009 | Jerebko | G06T 17/20 382/128 |
| 2010/0069758 A1* | 3/2010 | Barnes | A61B 5/0059 600/473 |
| 2010/0142778 A1* | 6/2010 | Zhuo | G06T 5/50 382/128 |
| 2010/0185425 A1* | 7/2010 | Li | G06F 19/701 703/6 |
| 2011/0142316 A1* | 6/2011 | Wang | G06T 11/006 382/131 |
| 2016/0049284 A1 | 2/2016 | Stauber et al. | |

OTHER PUBLICATIONS

David M. Beazley et al., "Parallel algorithms for short-range molecular dynamics," 1995, Annual Reviews of Computational Physics III, World Scientific Publishing, pp. 119-121, 133-134, 137-139.*

International Search Report, dated Mar. 31, 2015, from corresponding PCT application.

* cited by examiner

METHOD FOR PROCESSING MOLECULAR IMAGING DATA AND CORRESPONDING DATA SERVER

TECHNICAL FIELD OF THE INVENTION

The present invention relates to a process for processing molecular imaging data based on the use of a high-volume database structure, as well as on the server of corresponding data. Molecular imaging generally covers all imaging techniques essentially observing molecular operation of organs and/or organisms ex vivo or in vivo by the least invasive means possible or the least disruptive possible of the observed biological or biophysical systems.

TECHNOLOGICAL BACKGROUND

Molecular imaging is experiencing a considerable upswing in the evolution of the number of technologies especially in mass spectrometry imaging (MSI), magnetic resonance imaging (MRI), or Raman spectrometry. These technologies are used to conduct studies in bio-distribution of targeted endogenic or exogenic compounds such as pesticides, drugs, proteins or lipids for studying their roles in biological systems. Applications of these technologies with competition from software also search for potential non-supervised bio-markers.

But, the increase in data to be analyzed and interpreted in molecular imaging constitutes a limitation for synthetic analyzes on several data sets each associated with an image. Data are becoming difficult to exploit for synthetic representations or to be analyzed statistically.

Indeed, the high volume of information of data sets is often greater than the size of the random access memory of conventional computers (as opposed to supercomputers). With mass spectrometry imaging for example, images of 50,000 positions can no longer store all the raw information in memory and therefore need to perform calculations to reduce impact on memory and allow exploitation of these images. Calculations reduce data and consequently cause bias by not considering all available information. Also, current analysis tools have no means for standardizing several data sets relative to each other.

There are many storage formats mainly linked to manufacturers of acquisition robots of data sets. However, none of these formats is adapted and optimized to be interrogated finely and rapidly. Some fields of molecular imaging have emphasized storage formats such as Analyze 7.5 found in MRI (Magnetic Resonance Imaging) and mass spectrometry imaging. Mass spectrometry imaging also contains the format iMZML which however does not constitute a storage system for handling imaging to data.

Formats of type HDFS ("Hierarchical Data Format 5") based on hierarchical organization of data have recently been used in the storage of high-volume data in mass spectrometry imaging. These formats build remote interrogation interfaces via Internet navigators. They enable faster statistical calculations than with non-hierarchized files. These formats however do not produce overall comparative and searchable analysis of data in studies of several data sets simultaneously.

There is therefore the need for a process for analyzing, comparing, and interrogating several data sets relative to each other without information loss so as to avoid introducing analysis bias.

SUBJECT OF THE INVENTION

The aim of the present invention is to respond effectively to this need by proposing a process for processing a plurality of spectral data sets, intended especially to be exploited by a molecular imaging process, each data set being defined by a set of spatial positions with each of which is associated a molecular spectrum of at least two dimensions containing a set of molecular information, characterized in that it includes especially the following steps:

for each data set, cutting the molecular spectrum associated with each position into several sections of molecular information, or sections of spectrum, each containing a reduced set of molecular information, inserting the sections obtained for each position of each data set into a database such that a set of indexed sections of spectrum is associated with each position of each data set, selecting in the database, following a request relative to molecular information of interest, the section(s) containing the molecular information of interest, and selecting within each section said molecular information of interest.

The invention also relates to a process for recording a plurality of spectral data sets during a molecular imaging process, each data set being defined by a set of spatial positions with each of which a molecular spectrum having at least two dimensions containing a set of molecular information is associated, characterized in that it includes the following steps:

during acquisition of spectral data, and for each spectral data set, cutting the molecular spectrum associated with each position into several sections of spectrum, each containing some of the molecular information of said spectrum, inserting the sections obtained for each position of each data set into a database such that a set of indexed sections of spectrum is associated with each position of each data set, and optionally selecting in the database following a request relative to molecular information of interest the section(s) containing the molecular information of interest, and selecting within each section said molecular information of interest.

More generally, the invention proposes processing data sets, acquired advantageously in an automated manner by cutting into sections the molecular spectra associated with each of the spatial positions of the sets of spatial positions making up said data sets. Corresponding to each spectrum is a succession of sections of spectrum, all comprising all of the molecular information of the associated spectrum. According to the invention the step of cutting into sections can be taken, advantageously in an automated manner, during acquisition of spectral data or during analysis of spectral data.

In a first embodiment the successive sections do not overlap and are simply adjacent such that no molecular information from a relevant spectrum is lost or redundant. In another embodiment some of the sections of a relevant spectrum can overlap partially so that some molecular information can be present in two successive sections of spectrum of a same spectrum.

The invention substantially reduces the loading period of data to be analyzed to the extent where it is possible to recover, by selection of sections, useful information in the database. It is also possible to cut the spectral data as soon as data are recorded, during their acquisition, such that the sections of spectral data are integrated directly during analysis of the sample by a molecular imaging process.

Due to cutting into sections of the signal, without reduction of the spectrum, the invention also works without reduction of information in terms of combined studies of pharmacokinetic, pharmacodynamic and quantification of endogenic or exogenic molecules in the same analysis to observe in their entirety physiological events such as screening methods (distribution comparison of several drug candidates), methods of quantification, methods of occupation study of receptors or tissue screening, metabolism or 3D reconstruction study. The invention also optimizes the use of memory necessary for statistical processing and representations of molecular data imaging on several data sets.

According to an embodiment, the process for data processing or recording of the invention includes the step of viewing the molecular information of interest in the form of a set of data maps, each corresponding to a data set.

Advantageously, the molecular spectra are cut out according to a determined pitch which can be identical or different from one spectrum to another.

According to an embodiment, the process for data processing or recording of the invention comprises the following steps:
  cutting all molecular information into sections of spectrum according to at least one predetermined pitch,
  inserting a reference axis setting up correspondence between points index of the different sections of spectrum and the corresponding molecular information, and
  selecting the spectrum section containing the molecular information of interest as a function of the reference axis and the predetermined pitch.

According to an embodiment, before or after insertion of sections in the database, said process includes at least one pre-processing step consisting of spectral alignment and/or subtraction of background noise and/or intra data set standardization.

According to an embodiment, the process for data processing or recording of the invention comprises the step of resizing the spatial positions of the data sets having different spatial sizes so as to be aligned on the data set having the finest spatial size.

According to an embodiment, the process for data processing or recording of the invention further includes the step of extracting a data set, such as maximum intensity, average intensity, an area under a peak, a noise-to-signal ratio of each peak of interest of all molecular information.

According to an embodiment, extraction is achieved as a function of peak selection criteria defined by a quality criterion of a noise-to-signal ratio and/or a spectral resolution.

According to an embodiment, the process for data processing or recording of the invention includes the step of standardizing the sets of molecular information of the plurality of the data sets to each other so as to then compare the different data sets to each other.

According to an embodiment, for undertaking the standardization step said process can comprise the following steps:
  selecting one reference molecule or several endogenic or exogenic reference molecules common to all of the data sets,
  calculating, for each data set, a standardization factor as a function of this or these reference molecule(s), and
  correcting the molecular information of interest with this standardization factor to obtain a set of standardized data sets.

According to an embodiment, the standardization factor is defined from at least one reference molecule present on a set of samples corresponding to the data sets or in a particular reference zone of the samples corresponding to the data sets.

According to an embodiment, the process for data processing or recording of the invention includes the step of viewing, comparing and analyzing, in the form of a plurality of data maps each coming from a standardized data set, the molecular information of interest with a color scale common to all of the maps.

According to an embodiment, the common color scale is based on the smallest and largest intensity of all the data sets for the molecule of interest.

According to an embodiment, said data sets are obtained by a mass spectrometry process.

According to an embodiment, said data sets are obtained by an imaging process of Positron Emission Tomography (PET) or Magnetic Resonance Imaging (MRI) type.

Advantageously, all or some of the recording and/or processing process steps according to the invention are automated.

Another aim of the invention is a data server including a memory storing software instructions for executing at least some of the steps of the process for processing a plurality of data sets according to the present invention.

Another aim of the invention is a data medium readable by computer comprising instructions executable by the computer and adapted to allow a computer system to execute at least one step of the process for processing or recording spectral data according to the invention.

Accordingly, the invention proposes a computer program comprising program code instructions for execution of all or some of the steps explained above when said program is run on a computer.

Advantageously, the computer program comprises program code instructions for execution of at least the step of cutting the molecular spectra into sections of spectrum.

BRIEF DESCRIPTION OF FIGURES

The invention will be more clearly understood from the following description and examination of the accompanying figures which are given by way of illustration only but non-limiting of the invention.

Identical, similar or analog elements retain the same references from one figure to the other.

DESCRIPTION OF AN EMBODIMENT OF THE INVENTION

The following example for executing the process according to the invention is described for a mass spectrometry method of MALDI type. Of course, a imaging device other than MALDI could be used substantially identically, such as for example the sources: SIMS, DESI, LAESI, DIOS, ICP, Microscope MALDI, SNOM, SMALDI, LA-ICP, ESI (liquid extraction on tissue), MILDI, JEDI, ELDI etc. The process also applies to any other method for producing data exploitable by a method of molecular imaging such as for example PET ("Positron Emission Tomography") or MRI (Magnetic Resonance Imaging).

Figure 1:
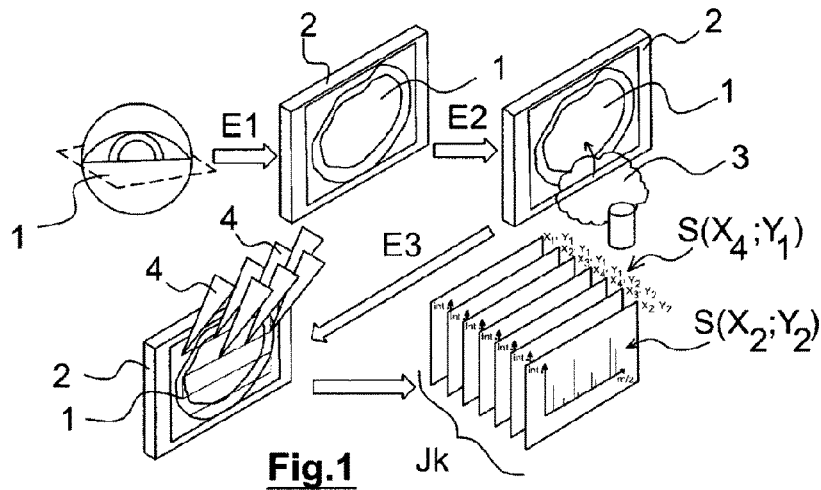
FIG. 1 schematically illustrates the different steps of a mass spectroscopy process for obtaining data sets exploited by the process according to the present invention.

FIG. 1 schematically illustrates the different steps performed by a MALDI mass spectrometry process. A first step E1 consists of cutting out, in general by cryo-section, a tranche of tissue 1 which is then placed on a slide 2. In a step E2 a fine uniform layer of ionizing matrix 3 is then deposited on the tranche of tissue 1. Acquisition step E3 consists of generating automated laser pulses 4 having a predefined size, for example of the order of 100 micrometers per acquisition zone, to ionize the molecules of the matrix 3. The molecules ionized in this way are analyzed as is known per se by a mass spectrometer. Reference could be made to document FR2973112 for more details on carrying out the process.

A data set Jk is produced, defined by a set of spatial positions (Xi, Yj) associated with each of which is a set of molecular information. The spatial positions are defined as a function of a reference referential of axes X and Y. All the molecular information is formed in this case especially by a spectrum S having two dimensions indicating intensity as a function of molecular mass. For example, the data set Jk obtained has 50,000 intensities (or 50,000 points) per spectrum over 20,000 spatial positions Xi, Yj. The process according to the invention is based on processing a plurality of data sets J1-Jn.

Figure 3:
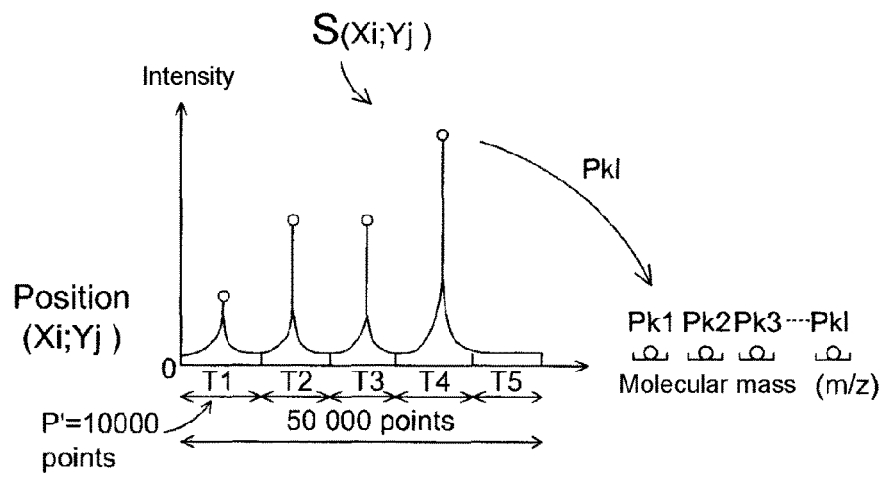
FIG. 3 is a schematic illustration of the step for obtaining the spectra sections associated with each position of a data set.

As is shown in FIG. 3, for each data set Jk likely to be shown in the form of an image, the molecular spectrum S(Xi, Yj) associated with each position (Xi, Yj) is cut into several sections of spectra T1-Tm. The sections T1-Tm are cut out as per a predetermined pitch P'. For example, for each spectrum of 50,000 points per spatial position, each spectrum could be cut as per a pitch P' of 10,000 points. Or, the spectrum S(Xi, Yj) is cut into five sections T1-T5 of 10,000 points each. As a variant, the pitch P' used could be variable.

Figure 4:
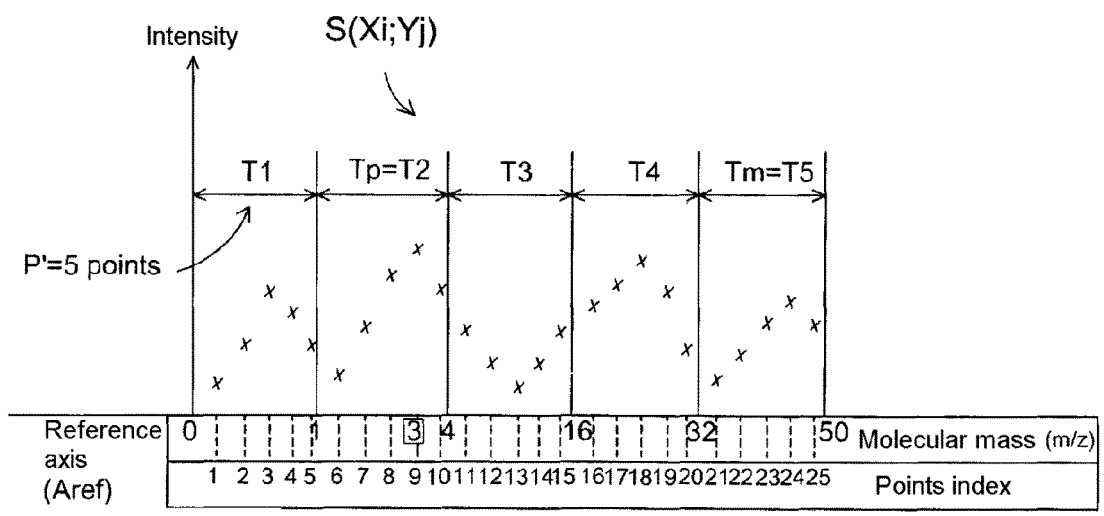
FIG. 4 shows the steps for setting up correspondence between molecular information and the corresponding spectrum section.

A reference axis Aref, shown in FIG. 4 is also defined, setting up correspondence between points index of different sections T1-Tm and the corresponding molecular mass.

Before insertion into a database BDD the process preferably performs at least one pre-processing step of spectra S(Xi, Yj) via a module 100. This pre-processing step could consist of spectral alignment. For this purpose reference peaks are considered and the spectrum is offset so as to position the values of corresponding peaks on these reference peaks. It will also be possible to perform subtraction of background noise by readjusting the spectrum as a function of a distance between the minimum value of the spectrum and a reference value to which the minimum value of the spectrum would have to correspond.

Furthermore, different types of signal standardization (internal standardization) could be carried out (by an internal standard, by use of the total of intensities . . . ). In other words, intra data set standardization is performed here, i.e, standardization for each data set independently of the other data sets, which corresponds to steps known per se to the skilled person. This intra data set standardization is performed as a complement to subsequent standardization steps between the data sets J1-Jn detailed hereinbelow (inter data set standardization) which will precisely and securely compare the data sets J1-Jn to each other.

Also, the process includes the step of extracting a data set, such as maximum intensity Pk1-Pkl, average intensity, an area under a peak, a noise-to-signal ratio of each peak of interest of the spectra S(Xi, Yj). It is possible to extract the maximum intensity of each peak Pk1-Pkl of the spectrum S(Xi, Yj) according to a method called "PeakPicking". Extraction is done as a function of peak selection criteria defined by a quality criterion of the noise-to-signal ratio and/or the spectral resolution.

Figure 2:
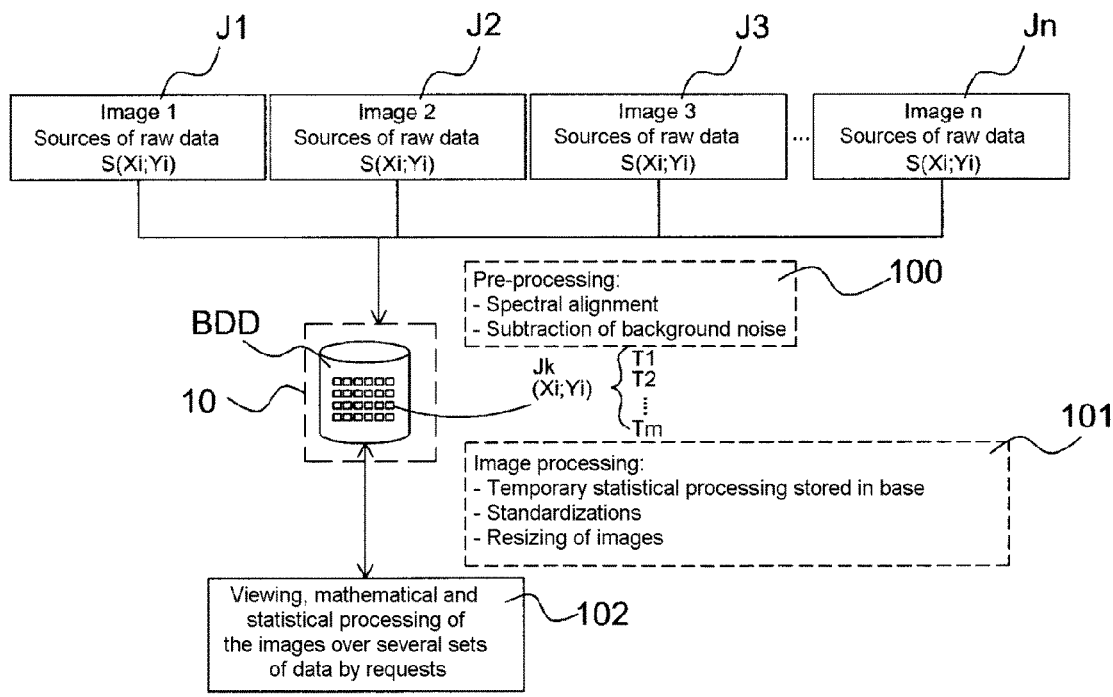
FIG. 2 is a synoptic chart of the integrated database management system for execution of the process for processing data according to the present invention.

The sections T1-Tm obtained for each position (Xi, Yj) of each data set J1-Jn as well as the reference axis Aref and the peaks Pk1-PKl previously extracted are inserted into the database BDD as is shown in FIG. 2. In this way, a set of indexed sections T1-TM and a set of peaks Pk1-PKl and abovementioned complementary data (average intensities, areas of each peak) are associated with each position (Xi, Yj) of each data set J1-Jn.

The database BDD is a high-volume database of NoSQL ("Not only Structured Query Language") or SQL type enabling viewing, management, interpretation and statistical analysis of inserted data. The database management system can for example be selected from the following non-exhaustive systems: Hypertable, Haddoop, Cassandra, MongoDB, PolyBase, Hadoop on Azure, Hive, Pig. The database system ensures coherence, reliability, and pertinence of data. Techniques for replication and saving can ensure reliability of information.

The steps for selection of pertinent information in the database BDD are described below. Following a request relative to molecular information of interest, the section(s) of the positions of the sets of data set J1-Jn containing the requested molecular information is selected. For this purpose, for each position Xi, Yj of each data set J1-Jn, the section Tp containing the requested molecular information is selected as a function of the reference axis Aref and the requested molecular information.

Therefore, FIG. 4 illustrates cutting of a spectrum into sections according to a pitch P' of five points for easier comprehension of this step. As is often the case for spectra originating from a mass spectrometry method, the scale of the molecular masses is not linear. In the event where the user requires information relative to a molecule having for example a molecular mass of value 3 m/z, the reference axis Aref stipulates that the index of the point corresponding to this value of molecular mass is 9, such that it can be deduced by means of the pitch P' that the section Tp containing the intensity of the molecular mass of interest is the second section T2.

Alternatively, a table which stores minimum and maximum terminals of the molecular masses and indexation of the points of each corresponding section T1-Tm can be used. In this case, for requested molecular information, the identifier of the section T1-Tm is selected as a function of these minimum and maximum terminals.

Within each section T1-Tm selected for each of the points of all the data sets J1-Jn, the corresponding intensity of the requested molecular mass is then selected. It then becomes possible to view, in the form of a set of data maps C1-CN each corresponding to a data set J1-Jn, the distribution of the intensity of presence of the molecule of interest on the different maps C1-CN. A color is attributed as a function of the intensity of the molecular information on a color scale. Alternatively, or by way of complement, extraction of peaks Pk1-PKl rapidly produces images providing initial analysis of the distribution of the intensity of a molecule of interest.

The process preferably includes the step of standardizing the molecular information of the data sets J1-Jn to then compare several data sets to each other (cf. module 101). For this purpose, a reference molecule Mref common to all the data sets J1-Jn is selected. Alternatively, several endogenic or exogenic molecules common to all of the data sets J1-Jn are selected. It is possible to consider the presence of the reference molecule(s) Mref in the complete samples or more specifically in a reference zone of the corresponding samples.

More precisely, for each data set J1-Jn, a standardization factor Fnor is calculated as a function of this or these reference molecule(s) Mref. The molecular information of interest is then corrected with this standardization factor Fnor to produce a data set of standardized sets J1-Jn.

Figure 5:
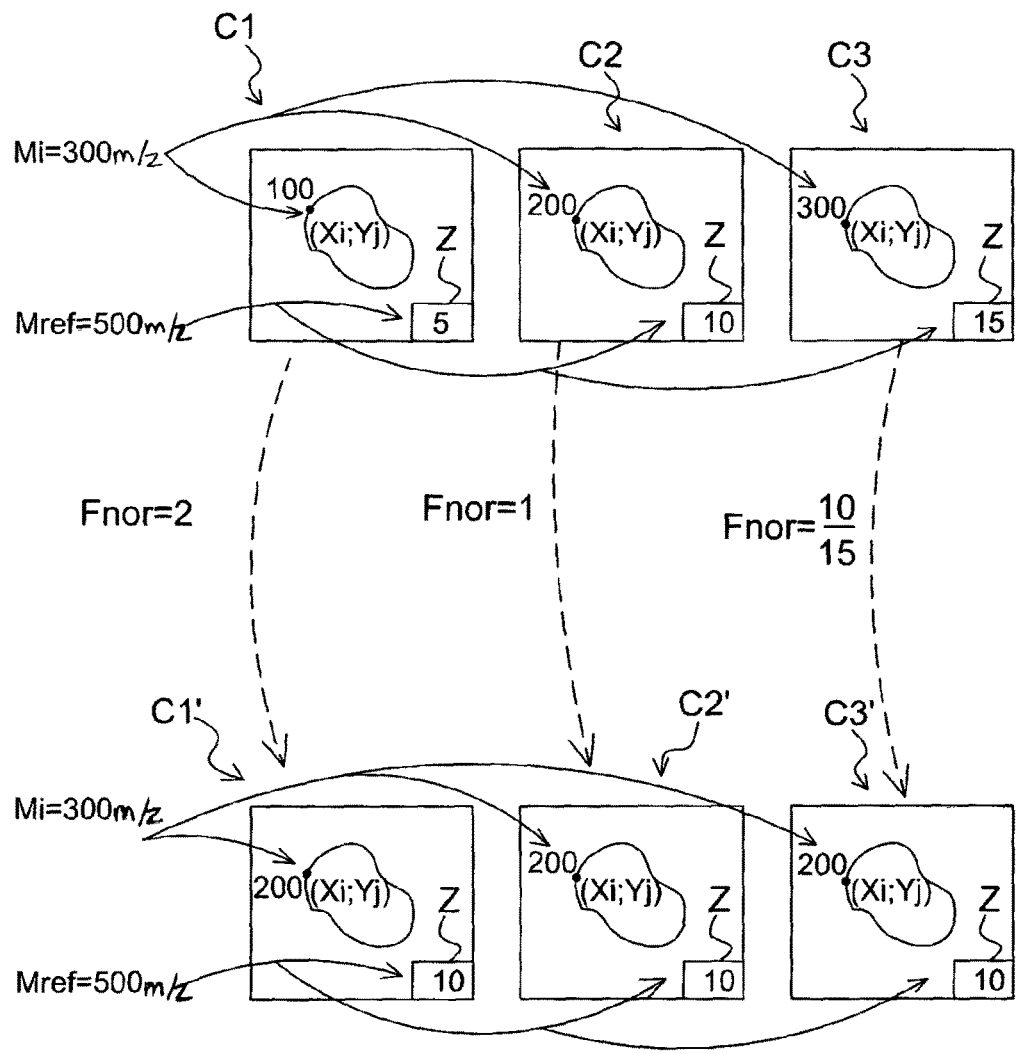
FIG. 5 schematically illustrates the inter-image standardization steps for precisely comparing several images.

For example, for three data sets corresponding to the maps C1-C3 shown in FIG. 5 a reference molecule Mref=500 m/z is selected as standardizing molecule (standardizing standard). This molecule Mref respectively has a value of 5, 10 and 15 in the zone Z of the maps C1-C3. For each map C1-C3 a standardization factor Fnor is calculated on the basis of each of these values of Mref:

Fnor=Average of the values of Mref for C1-C3/value of the Mref of the relevant map. In the example shown in FIG. 5, a standardization factor Fnor respectively of 2, 1, and 10/15 for the maps C1, C2 and C3 is obtained. This coefficient is then applied to all of the intensity values of the spectra associated with the different positions of all the data sets J1-Jn and in particular the values of intensity of a molecule of interest Mi=300 m/z at the position Xi; Yj. Standardized maps C1'-C3' are obtained, which can be compared directly to each other.

Standardization corrects intensities linked to changes in experimental conditions due to the preparation of the sample and its analysis. In fact, in the preceding example it is evident that it would have been possible to arrive at an incorrect conclusion of a stronger presence of the molecule of interest Mi=300 m/z in the sample corresponding to the map C3, while after application of the standardization factor Fnor, study reveals a homogeneous presence of the molecule of interest Mi in the three samples with an intensity of 200 at the position Xi; Yj.

Following this standardization, it is possible to view, compare and analyze, in the form of standardized data maps C1'-C3', the molecular information with a color scale common to all of the maps C1'-C3' (cf. module 102). The scale obtained is based on the lowest and the highest intensity determined over all the data sets for the molecule of interest Mi.

Of course, it is possible to produce more than three data sets and corresponding maps for analyzing by statistical combining of several data sets J1-Jn transversely without need to load all into memory. The imaging data can then be compared to bring out potential markers. It is also possible to combine positions having common behavior to allow novel interpretation of data.

In other words, in a single tool, the invention compares and interrogates data to obtain more pertinent, standardized information the quality of which is quantifiable. Several data sets can be loaded with quality controls inserted into each of the images to standardize the data.

Furthermore, the process can if needed resize the positions of data sets J1 and J2 of the same biological sample having different spatial sizes so as to align with the data set having the finest spatial size. It is possible to combine the processing of a map coming from the mass spectrometer (imaging MALDI) with the processing of a map coming from a system of PET (Positron Emission Tomography) or MRI (Magnetic Resonance Imaging) type.

It is also possible to represent several data sets J1-Jn in codistribution in a single image. It is possible to conduct requests of the type which "select all the values v, w of all the positions x and y (of same spatial size) for the field z and a of the current map". Fields z and a represent the values of two different imaging technologies.

It is also possible to perform temporary statistic processing which could be added by insertion requests into the database BDD. In this way, the process according to the invention offers major flexibility to the extent where it is possible to add information on each position of the image at any moment of the analysis process.

The process is based on client/server architecture. The database BDD can be interrogated by a single interface. The datum is stored and interrogated in single-user architecture or in a cluster of servers accessible locally or via a network (internal or external). The client interface software can be installed at the workstation or in a web interface version. Another aim of the invention is the data server 10 including a memory storing software instructions for performing at least some of the steps of the process for processing a plurality of data sets J1-Jn.

Also, the processed number of data can easily grow such that the amount of the datum to be analyzed is no longer a limitation to analysis. The insertion of data is effective irrespective of the size of the database BDD.

Of course, the above description has been given by way of example only and does not limit the field of the invention and replacing the execution details by all other equivalents would not exceed its scope.

The invention claimed is:

1. A process for processing a plurality of spectral data sets (J1-Jn) intended to be exploited by a molecular imaging process, each spectral data set (J1-Jn) being defined by a set of spatial positions (Xi, Yj) with each of which is associated a molecular spectrum of at least two dimensions containing a set of molecular information (S(Xi, Yj)), the process comprising the following steps:

acquiring the spectral data sets from an analytical method, for each data set (J1-Jn) cutting the molecular spectrum associated with each position (Xi, Yj) into several sections of spectrum (T1-Tm) each containing some of the molecular information of said spectrum, inserting the sections (T1-Tm) obtained for each position (Xi, Yj) of each data set (J1-Jn) into a database (BDD), such that a set of indexed sections of spectrum (T1-Tm) is associated with each position (Xi, Yj) of each data set (J1-Jn), selecting in the database (BDD) following a request relative to molecular information of interest, the section(s) (T1-Tm) containing the molecular information of interest, selecting within each section (T1-Tm) said molecular information of interest, cutting the molecular spectra (S(Xi, Yj)) into sections of spectrum (T1-Tm) as per at least one predetermined pitch (P'), inserting a reference axis (Aref) setting up correspondence between points index of the different sections (T1-Tm) and the corresponding molecular information, selecting the section (T1-Tm) containing the molecular information of interest as a function of the reference axis (Aref) and of the predetermined pitch (P'), and viewing and analyzing the molecular information of interest in the form of a set of data maps (C1-Cn), each corresponding to a data set (J1-Jn).

2. A process for recording a plurality of spectral data sets during a molecular imaging process, each data set being defined by a set of spatial positions, with each of which is associated a molecular spectrum of at least two dimensions containing a set of molecular information, the process comprising the following steps:

acquiring spectral data and the spectral data sets from an analytical method, during the acquisition of the spectral data, and for each spectral data set, cutting the molecular spectrum associated with each position into several sections of spectrum, each containing some of the molecular information of said spectrum, inserting the sections obtained for each position of each data set into a database such that a set of indexed sections of spectrum is associated with each position of each data set, and optionally selecting in the database, following a request relative to molecular information of interest, the section(s) containing the molecular information of interest, selecting within each section said molecular information of interest, cutting the molecular spectra (S(Xi, Yj)) into sections of spectrum (T1-Tm) as per at least one predetermined pitch (P'), inserting a reference axis (Aref) setting up correspondence between points index of the different sections (T1-Tm) and the corresponding molecular information, selecting the section (T1-Tm) containing the molecular information of interest as a function of the reference axis (Aref) and of the predetermined pitch (P'), and viewing and analyzing the molecular information of interest in the form of a set of data maps (C1-Cn), each corresponding to a data set (J1-Jn).

3. The process according to claim 1, wherein, before or after insertion of sections (T1-Tm) into the database (BDD) said process includes at least one pre-processing step consisting of spectral alignment and/or subtraction of background noise and/or intra data set standardization (J1-Jn).

4. The process according to claim 1, which includes the step of resizing the spatial positions (Xi, Yj) of the data sets (J1-Jn) having different spatial sizes so as to be aligned on the data set (J1-Jn) having the finest spatial size.

5. The process according to claim 1, which further includes the step of extracting maximum intensity (Pk1-Pkl), average intensity, an area under a peak, a noise-to-signal ratio of each peak of interest of all the molecular spectra.

6. The process according to claim 5, wherein extraction is performed as a function of peak selection criteria defined by a quality criterion of a noise-to-signal ratio and/or a spectral resolution.

7. The process according to claim 1, which includes the step of standardizing the molecular spectra of the plurality of the data sets (J1-Jn) to each other so as to then compare the different data sets (J1-Jn) to each other.

8. The process according to claim 7, wherein to perform the standardization step, said process includes the following steps:

selecting a molecule or several endogenic or exogenic reference molecules (Mref) common to all of the data sets (J1-Jn), calculating, for each data set (J1-Jn), a standardization factor (Fnor) as a function of this or these reference molecules (Mref), and correcting the molecular information of interest with this standardization factor to obtain a set of standardized data sets (J1-Jn).

9. The process according to claim 8, wherein the standardization factor (Fnor) is defined from at least one reference molecule (Mref) present on a set of samples corresponding to the data sets (J1-Jn) or in a particular reference zone (Z) of the samples corresponding to the data sets (J1-Jn).

10. The process according to claim 7, which includes the step of viewing, comparing and analyzing, in the form of a plurality of data maps (C1'-Cn') each coming from a standardized data set (J1-Jn), the molecular information of interest with a color scale common to all of the maps.

11. The process according to claim 10, wherein the common color scale is based on the smallest and largest intensity of all the data sets (J1-Jn) for the molecule of interest.

12. The process according to claim 1, wherein said data sets (J1-Jn) are obtained by a mass spectrometry process.

13. The process according to claim 1, wherein said data sets (J1-Jn) are obtained by an imaging process of Positron Emission Tomography (PET) or Magnetic Resonance Imaging (MRI) type.

14. A data server (10) including a memory storing software instructions for performing at least some of the steps of the process for processing a plurality of data sets (J1-Jn) defined according to claim 1.

15. The process according to claim 2, further comprising a step of viewing the molecular information of interest in the form of a set of data maps (C1-Cn) each corresponding to a data set (J1-Jn).

16. The process according to claim 2, wherein, before or after insertion of sections (T1-Tm) into the database (BDD) said process includes at least one pre-processing step consisting of spectral alignment and/or subtraction of background noise and/or intra data set standardization (J1-Jn).

17. The process according to claim 2, which includes the step of resizing the spatial positions (Xi, Yj) of the data sets (J1-Jn) having different spatial sizes so as to be aligned on the data set (J1-Jn) having the finest spatial size.

18. A process for processing a plurality of spectral data sets (J1-Jn) intended to be exploited by a molecular imaging process, each spectral data set (J1-Jn) being defined by a set of spatial positions (Xi, Yj) with each of which is associated a molecular spectrum of at least two dimensions containing a set of molecular information (S(Xi, Yj)), the process comprising the following steps:

acquiring the spectral data sets from at least one analytical method selected from mass spectrometry, positron emission tomography or magnetic resonance imaging, for each data set (J1-Jn) cutting the molecular spectrum associated with each position (Xi, Yj) into several sections of spectrum (T1-Tm) each containing some of the molecular information of said spectrum, inserting the sections (T1-Tm) obtained for each position (Xi, Yj) of each data set (J1-Jn) into a database (BDD), such that a set of indexed sections of spectrum (T1-Tm) is associated with each position (Xi, Yj) of each data set (J1-Jn), selecting in the database (BDD) following a request relative to molecular information of interest, the section(s) (T1-Tm) containing the molecular information of interest, selecting within each section (T1-Tm) said molecular information of interest, cutting the molecular spectra (S(Xi, Yj)) into sections of spectrum (T1-Tm) as per at least one predetermined pitch (P'), inserting a reference axis (Aref) setting up correspondence between points index of the different sections (T1-Tm) and the corresponding molecular information, selecting the section (T1-Tm) containing the molecular information of interest as a function of the reference axis (Aref) and of the predetermined pitch (P'), and viewing and analyzing the molecular information of interest in the form of a set of data maps (C1-Cn), each corresponding to a data set (J1-Jn).

\* \* \* \* \*